United States Patent
Hattori et al.

(10) Patent No.: US 9,451,779 B2
(45) Date of Patent: Sep. 27, 2016

(54) LEFT/RIGHT DETERMINATION SYSTEM FOR ARM PART OF PIG CARCASS

(71) Applicant: MAYEKAWA MFG. CO., LTD., Tokyo (JP)

(72) Inventors: Kazuhiro Hattori, Tokyo (JP); Masaru Tokumoto, Tokyo (JP); Hiroaki Muranami, Tokyo (JP)

(73) Assignee: MAYEKAWA MFG. CO., LTD., Tokyo (JP)

( * ) Notice: Subject to any disclaimer, the term of this patent is extended or adjusted under 35 U.S.C. 154(b) by 0 days.

(21) Appl. No.: 14/435,518

(22) PCT Filed: Oct. 23, 2012

(86) PCT No.: PCT/JP2012/077376
§ 371 (c)(1),
(2) Date: Apr. 14, 2015

(87) PCT Pub. No.: WO2014/064773
PCT Pub. Date: May 1, 2014

(65) Prior Publication Data
US 2015/0257396 A1    Sep. 17, 2015

(51) Int. Cl.
| A22C 17/00 | (2006.01) |
| A22B 7/00  | (2006.01) |
| G01N 21/27 | (2006.01) |
| G01N 23/04 | (2006.01) |
| G01N 21/25 | (2006.01) |

(52) U.S. Cl.
CPC ........... *A22B 7/003* (2013.01); *A22C 17/0073* (2013.01); *G01N 21/251* (2013.01); *G01N 21/27* (2013.01); *G01N 23/04* (2013.01); *G01N 2201/12* (2013.01)

(58) Field of Classification Search
CPC ...... A22C 25/00; A22C 25/08; A22C 25/18; A22C 17/0086; A22C 17/0073; A22C 17/008; A22C 17/0093; A22C 17/0046

USPC .................................................. 452/155–158
See application file for complete search history.

(56) References Cited

U.S. PATENT DOCUMENTS 5,902,177 A * 5/1999 Tessier ............... A22C 17/0046
                                                       452/156
5,944,598 A * 8/1999 Tong ....................... A22B 5/007
                                                       382/100

(Continued)

FOREIGN PATENT DOCUMENTS

EP    2153727 A1   2/2010
JP    06324006 A   11/1994

(Continued)

OTHER PUBLICATIONS

International Search Report issued in PCT/JP2012/077376, dated Jan. 15, 2013.

(Continued)

*Primary Examiner* — Richard Price, Jr.
(74) *Attorney, Agent, or Firm* — Rossi, Kimms & McDowell LLP

(57) ABSTRACT

An apparatus is disclosed for left/right determination of the arm part of a pig carcass before it is deboned. A plurality of clampers move around on an endless track. At a suspension station, a work is suspended from each clamper. There are left/right and front/back determination stations where it is determined whether a left-side or right side, and a front-side portion or back-side portion is facing a side irradiated by X-rays. Based on results of the determinations, posture of the work is corrected by a clamper rotating device. At an X-ray imaging station, it is controlled so that the front-side portion of the work faces the side irradiated by the X-rays and a longer side faces a movement direction of the endless track. An X-ray image of the work is obtained to determine a target coordinate of a bone-part surface required for incision making and deboning processes.

7 Claims, 8 Drawing Sheets

(56) References Cited

U.S. PATENT DOCUMENTS

| | | | | |
|---|---|---|---|---|
| 7,039,220 B2* | 5/2006 | Kriesel | ............... | G01B 11/25 382/110 |
| 7,399,220 B2* | 7/2008 | Kriesel | ............... | A01K 11/008 452/157 |
| 8,758,099 B2* | 6/2014 | Reifenhaeuser | ..... | A22C 17/002 452/157 |

FOREIGN PATENT DOCUMENTS

| JP | 2002281891 A | 10/2002 |
|---|---|---|
| JP | 2012056287 A | 3/2012 |
| WO | 2008096754 A1 | 8/2008 |

OTHER PUBLICATIONS

International Preliminary Report on Patentability issued in PCT/JP2012/077376, dated Apr. 28, 2015. Form PCT/IB/338 and PCT/IB/373.

Written Opinion issued in PCT/JP2012/077376, dated Jan. 22, 2013. Form PCT/ISA/237.

Extended European Search Report issued in European Application No. EP12887195.1 mailed Jun. 1, 2016.

* cited by examiner

Fig.9A
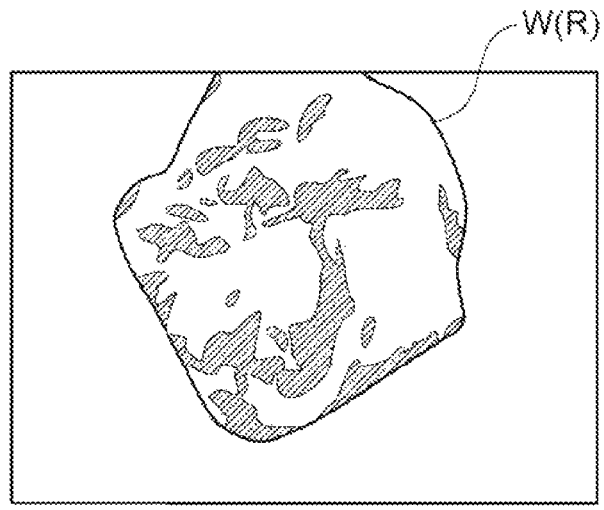
Fig.9B
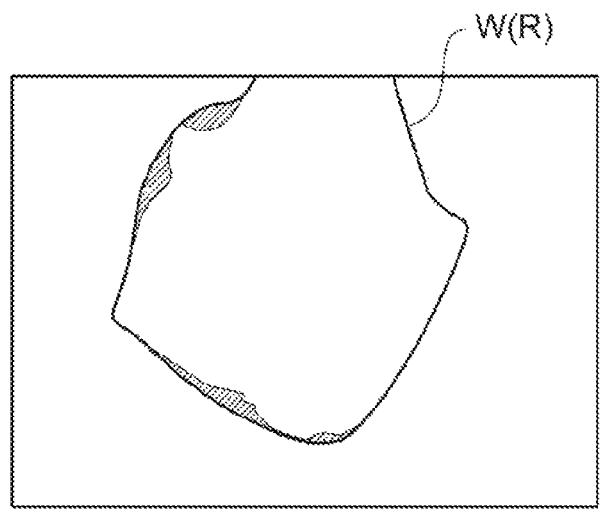
Fig.10
SIGNAL 1; LEFT, FRONT
SIGNAL 2; LEFT, BACK
SIGNAL 3; RIGHT, FRONT
SIGNAL 4; RIGHT, BACK
SIGNAL 5; NO WORK

LEFT/RIGHT DETERMINATION SYSTEM FOR ARM PART OF PIG CARCASS

TECHNICAL FIELD

The present invention relates to a left/right determination system for an arm part of a pig carcass suitably applied to a deboning apparatus or the like for an arm part of a pig carcass.

BACKGROUND

In the case where a carcass of livestock such as a pig, a cow, or a sheep is served as meat, it is required to break down a carcass of livestock and to separate meat parts from bone parts, which is referred to as a deboning process. A deboning process performed by manpower is hard work. Thus, the process has been increasingly automated by machines. In recent years, there are some types of deboning process that are automated in most parts except for pre-processing, depending on the kind of bone-in meat. In an automated deboning apparatus, for instance, a piece of bone-in meat to be processed is deboned while being conveyed in a state of being suspended from a clamper. In a deboning process of an arm part or a thigh part of a carcass of live stock, the shape of the arm part or the thigh part varies between the left and right sides of a carcass. Thus, a deboning process with high yields may not be performed if left/right determination is not performed beforehand. As the case may be, an error in the left/right determination may lead to an event in which operation of the deboning apparatus needs to be stopped.

The applicant has developed automatic deboning techniques for a carcass of livestock, including deboning processes for such an arm part and a thigh part. For example, Patent Document 1 discloses a deboning technique for a thigh part of a carcass of livestock. Patent Document 1 discloses a left/right determination method for a thigh part, which is to be performed as a previous step before the deboning process. This left/right determination method is for a thigh part after its haunch bone is removed by pre-processing. The method utilizes the position of a pocket that is formed on a bottom part after removing a haunch bone, the position being different between a left thigh part and a right thigh part, to determine whether a thigh part is from the left side or the right side of a carcass by detecting the position of the pocket using a sensing plate.

CITATION LIST

Patent Literature

Patent Document 1: WO2008/096754A

SUMMARY

Technical Problem

However, the method of left/right determination disclosed in Patent Document 1 utilizes the shape of a thigh part and thus it is not suitable to be applied to left/right determination for an arm part. Also, from the perspective of improving efficiency of the deboning process, it is desirable to enable left/right determination while an arm part is being suspended from a clamper.

In view of the problem of the prior art, an object of the present invention is to enable left/right determination while an arm part is being suspended from a clamper in a previous step before a deboning process upon deboning an arm part of a pig carcass that is widely served as meat, and to improve efficiency of the deboning process.

Solution to Problem

In order to achieve the above object, a left/right determination system for an arm part of a pig carcass of the present invention includes: a clamper including a slit which has an opening oriented in a horizontal direction so that a wrist part of a pig carcass is insertable into or removable from the slit, the clamper being configured to be movable along a track in a state where the arm part of the pig carcass is suspended from the clamper; a light source configured to radiate white visible light on the arm part suspended from the clamper; a color imaging device configured to capture an image of the arm part being irradiated with the white visible light from an inclined horizontal direction which is inclined relative to the horizontal direction in which the opening of the slit is oriented; and a left/right determination device configured to determine whether the arm part is of a left arm or a right arm based on an image data of the arm part captured by the color imaging device. In the present specification, white visible light means a visible light that is not separated into visible lights that have different wavelengths and colors. From the clamper, an arm part of a pig carcass is suspended at random without discriminating between left arm parts and right arm parts.

The present inventors and the like have found a phenomenon in which an arm part suspended from a clamper via a wrist part naturally rotates toward a direction that varies between left arm parts and right arm parts. The present invention utilizes this phenomenon and disposes the color imaging device at the position where different imaging areas can be obtained for left and right arm parts due to the natural rotation of the left and right arm parts toward different directions. As a result, left/right determination is enabled owing to the difference in the imaging areas.

The left/right determination device includes: an output extracting part configured to extract red image signals which correspond to a red wavelength range from the captured image data of the arm part of the pig carcass; a first binarizing part configured to binarize the red image signals extracted by the output extracting part; and a left/right determination part configured to determine whether the arm part is of a left arm or a right arm based on the red image signals binarized by the first binarizing part. The red image signals are, for instance, the R (red) image signals in the RGB representation type, and the M (magenta) image signals or the Y (yellow) image signals in the CMY representation type.

The output extracting part can extract red image signals by techniques such as dividing an image captured by the color imaging device into the three primary colors of R (red), G (green), and B (blue), or into C (cyan), M (magenta), and Y (yellow). An image data including the red image signals are used here, because the non-red image signals such as the G image signals, B image signals and C image signals cause meat parts (lean meat parts and fat parts) to appear dark and thus are not suitable for the binarizing. With the red image signals included, it is possible to perform left/right determination even if an image data of other color representation type is included. This left/right determination device enables accurate left/right determination for an arm part. According to the present invention, it is possible to perform left/right determination on an arm part of a pig carcass accurately while the arm part is being suspended from a clamper. Thus, it is possible to improve processing efficiency of the deboning apparatus.

According to the present invention, the opening of the slit of the clamper may be oriented in a direction orthogonal to the track while the color imaging device is capturing the image, and the inclined horizontal direction from which the color imaging device is configured to capture the image may form an angle of not less than 15° and not greater than 55° with respect to the track. When an arm part of a pig carcass is suspended from the clamper via a wrist part, the cross-sectional shape of the wrist part faces different directions for a left arm part and a right arm part. The present inventors and the like have found that, when a left arm part and a right arm part are each suspended via a wrist part from a clamper having a slit opening in a direction orthogonal to the track that is straight in the planar view, the arm parts naturally rotate toward opposite directions with respect to the track in the planar view in the range of [35±20]°. Accordingly, by capturing an image of an arm part of a pig carcass by the color imaging device disposed in this range of angles, it is possible to capture an image whose image area is clearly different for a left arm part and a right arm part.

In the present invention, the output extracting part can extract non-red image signals which correspond to a wavelength range other than the red wavelength range from the image data. Also, the left/right determination device may further include: a second binarizing part configured to binarize the non-red image signals extracted by the output extracting part; and a front/back determination part configured to determine whether a front side or a back side of the arm part is facing the color imaging device based on a distribution of the non-red image signals binarized by the second binarizing part. The non-red image signals are, for instance, the G image signals or the B image signals in the RGB representation type, and the C image signals in the CMY representation type.

In the present specification, in an arm part of a pig carcass, a root portion side adjacent to a shoulder part is a back-side portion where a meat part is exposed, and a portion on the opposite side of the back-side portion is a front-side portion where a meat part is not exposed. For the back-side portion where the red meat part is exposed, the non-red image signals outputted from the output dividing part is clearly reduced compared to the front-side portion. Also, in the image outputted from the second binarizing part, a region with many red image signals is enlarged. The front/back determination part utilizes this phenomenon to enable accurate determination of whether the image captured by the color imaging device is of a front-side portion or a back-side portion.

There are a case where skin is still adhering on the front-side portion and a case skin is removed from the front-side portion, depending on the way of pre-processing before the deboning process. In the case where skin is removed, fat under the skin is exposed. Since fat has a whitish color, the non-red image signals of the front-side portion are substantially the same regardless of whether there is skin or not. Accordingly, regardless of the presence of skin, it is possible to distinguish between a front-side portion and a back-side portion, and thus to perform accurate front/back determination. By combining the left/right determination part and the front/back determination part, it is possible to perform the left/right determination and front/back determination on an arm part at the same time. As a result, when applied to a deboning apparatus, left/right determination for an arm part and direction determination for an arm part can be accurately obtained, which enables accurate incision making in the downstream process. Accordingly, it is possible to perform a deboning process with high yields of meat parts.

In the present invention, the left/right determination system may further include: a suspending device configured to suspend the arm part from the clamper at an upstream position relative to a position where the color imaging device captures the image; a detector configured to detect whether the arm part is suspended from the clamper; and a first control device configured to cause the color imaging device to start to capture the image of the arm part upon receiving a suspension signal transmitted from the detector. As a result, it is possible to start to capture an image of an arm part by the color imaging device in accordance with the time when the arm part has been suspended from the clamper, which makes it possible to start the left/right determination step at an appropriate timing and immediately.

In the present invention, the left/right determination system may further include: an X-ray imaging device configured to radiate an X-ray on the arm part to obtain an X-ray image at a downstream position relative to the position where the color imaging device captures the image; a clamper rotating device configured to rotate the clamper about a vertical axial line between the position where the color imaging device captures the image and a position where the X-ray imaging device captures the image; and a second control device configured to set a target value of a rotation angle based on a result of left/right determination of the arm part determined by the left/right determination device to drive the clamper rotating device so that the clamper is rotated by the set target value.

With the above configuration, a natural rotation angle of an arm part is obtained in advance to be used as a target value. As a result, it is possible to orient the arm part, which is inclined with respect to the track due to the natural rotation, to face directly into the X-ray irradiating direction in which the X-ray is radiated. Here, "to orient the arm part to face directly into the X-ray irradiating direction of the X-ray imaging device" means to orient a longer side of the arm part to a direction substantially orthogonal to the X-ray irradiating direction and to orient one of the front-side portion or the back-side portion which can undergo the deboning process in the downstream process to face the side irradiated by the X-ray. If the arm part is not oriented to the direction orthogonal to the X-ray irradiating direction, the X-ray may not go through the arm part and thus a sharp transmission image may not be obtained. Also, if a portion of a predetermined side of the front-side portion or the inner-side portion is not oriented to the side irradiated by the X-ray, the deboning process may not be performed.

The second control device may be configured to set a target value of a rotation angle based on the result of left/right determination and a result of front/back determination determined by the left/right determination device to drive the clamper rotating device so that the clamper is rotated by the set target value. As a result, by rotating the clamper based on the result of front/back determination in addition, it is possible to orient the arm part accurately to face directly into the X-ray irradiating direction of the X-ray imaging device.

Further, the left/right determination system may further include a true/false determination device configured to determine whether the results determined by the left/right determination device are true or false based on a direction of the clamper and a direction of the arm part in the X-ray image obtained by the X-ray imaging device. As described above, a left arm part and a right arm part after being suspended from the clamper naturally rotate in different directions with respect to the track of the clamper. Thus, on a side immediately upstream relative to the X-ray imaging device, a left arm part and a right arm part are rotated to opposite directions to face directly into the X-ray irradiating direction. As a result, in the case where the result of left/right determination by the left/right determination device is false, the arm part may not face directly into the X-ray irradiating direction at the X-ray imaging device. The same applies to the case where the result of front/back determination is false.

As described above, it is possible to check whether the results of left/right determination and front/back determination are true or false from the directions of the clamper and the arm part in the X-ray image obtained by the X-ray imaging device. Thus, by processing the X-ray image by the true/false determination device to obtain the direction of the clamper and the direction of the arm part, it is possible to automatically judge whether the results of left/right determination and front/back determination are true or false. An arm part with a false result is not treated in the deboning step because an X-ray image required for the deboning process may not be obtained.

Advantageous Effects

According to the present invention, it is possible to perform accurate left/right determination of an arm part of a pig carcass while the arm part is being suspended from a clamper. Thus, it is possible to improve efficiency of a deboning process when applied to a deboning apparatus.

BRIEF DESCRIPTION OF DRAWINGS

FIG. 9A is an explanatory diagram of an image for front/back determination of a right arm part obtained by the deboning apparatus.

FIG. 9B is an explanatory diagram of an image for front/back determination of a right arm part obtained by the deboning apparatus.

FIG. 10 is a chart of determination results obtained by the deboning apparatus.

DETAILED DESCRIPTION

Embodiments of the present invention will now be described in detail with reference to the accompanying drawings. It is intended, however, that unless particularly specified, dimensions, materials, shapes, relative positions and the like of components described in the embodiments shall be interpreted as illustrative only and not limitative of the scope of the present invention.

Figure 1:
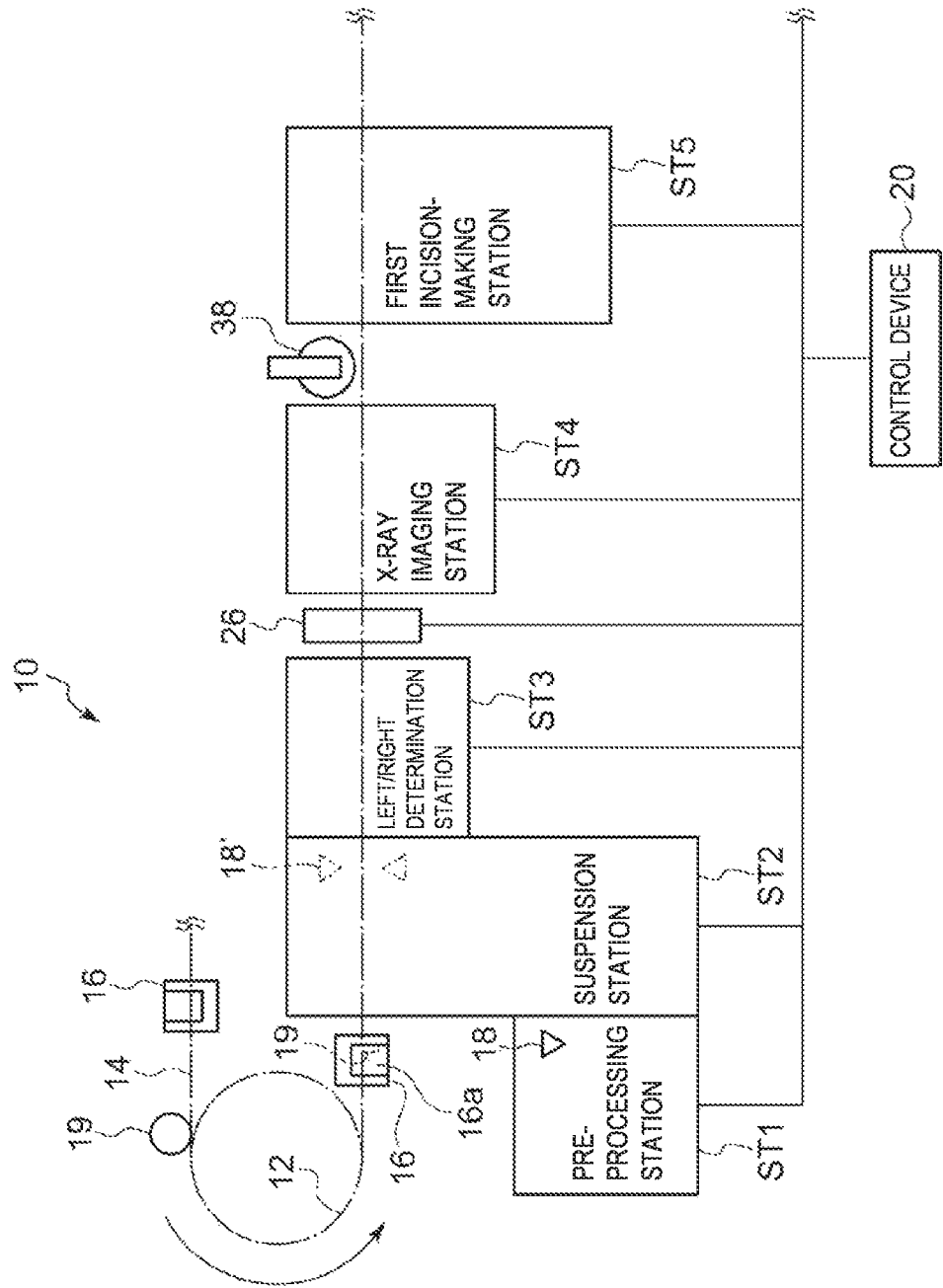
FIG. 1 is a configuration diagram of a deboning apparatus to which the present invention is applied according to one embodiment of the present invention.
Figure 2:
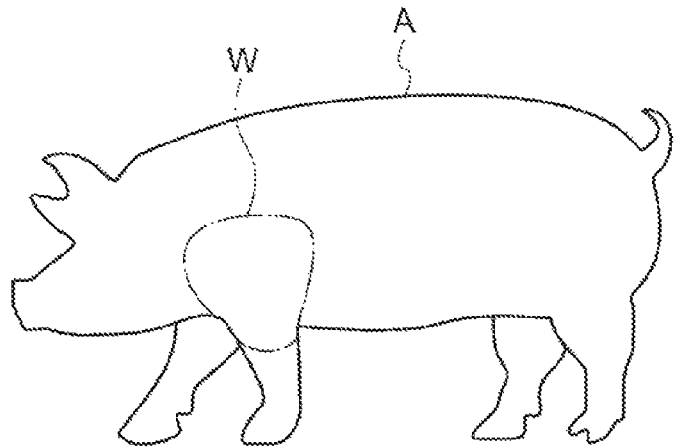
FIG. 2 is a diagram for describing an arm part of a pig.
Figure 3:
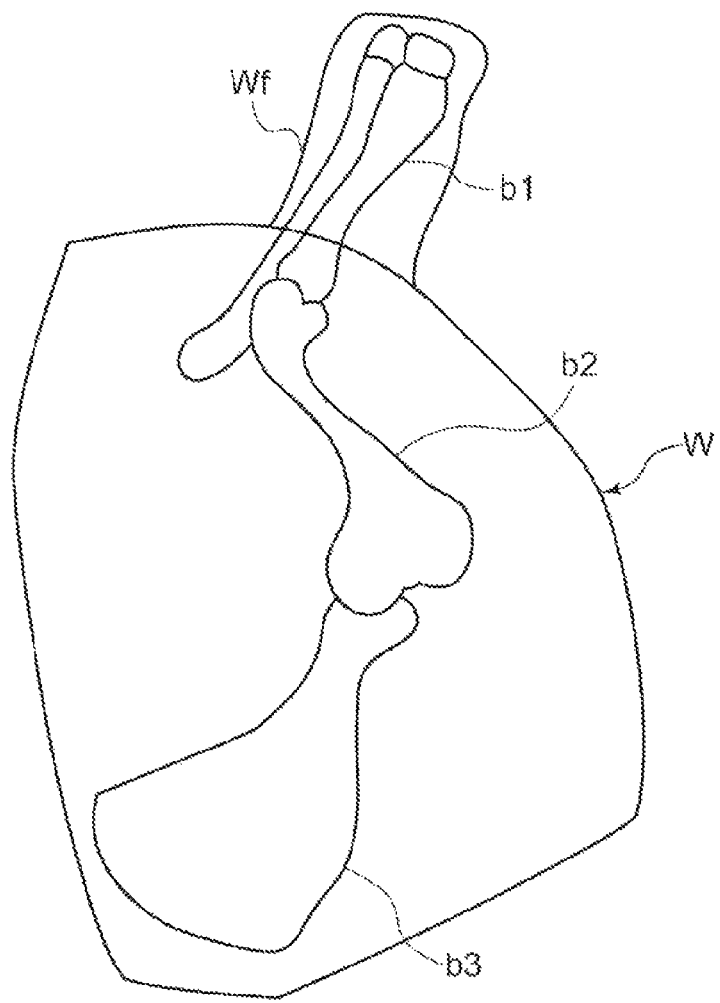
FIG. 3 is a schematic diagram of an arm part of a pig carcass.

An embodiment in which the present invention is applied to a deboning apparatus for an arm part of a pig carcass will be described in reference to FIGS. 1 to 10. FIG. 1 is a configuration diagram schematically illustrating a part of a deboning apparatus 10. As illustrated in FIG. 2, an arm part of a pig carcass (hereinafter, referred also to as a work and associated with a reference sign W) that undergoes a deboning process by the deboning apparatus 10 is a piece of bone-in meat including an arm part which is cut off from a trunk A of a pig. As illustrated in FIG. 3, a bone part of the work W includes a fore arm bone b1 that constitutes a wrist part Wf, an upper arm bone b2, and a shoulder blade b3.

As illustrated in FIG. 1, a conveyer that conveys the work W is disposed on a pre-processing station ST1. A portion on the tip end side with respect to the wrist part Wf of the work W is cut off on the conveyer, so that the wrist part Wf remains. The deboning apparatus 10 has an endless track 14 including a chain disposed around two sprockets 12 (one of which is omitted from the drawing). A plurality of clampers 16 are mounted to the chain with equal intervals, and the sprockets 12 rotate in the direction of the arrow to make each clamper move around on the endless track 14. A suspension station ST2 is disposed adjacent to the pre-processing station ST1. A 6-axis multi joint arm, for instance, is disposed on the suspension station ST2. A grip unit is disposed on an end of the multi-joint arm. The wrist part Wf of the work W is gripped by the grip unit and then suspended from the clamper 16. The work W is suspended so that its front-side portion faces outward from the endless track 14.

The clamper 16 includes a slit 16a into which the work W is to be inserted. The slit 16a is automatically closed by a chuck (not illustrated) disposed on the clamper 16 after the work W is inserted. The slit 16a is oriented to a direction that is outward from the endless track 14 and that is orthogonal to the endless track 14 in planar view when the work W is not being suspended. A photoelectric sensor 18 is disposed on a downstream end of the conveyer disposed in the pre-processing station ST1, and the photoelectric sensor 18 detects whether a work W is present.

The control device 20 includes, for instance, a computer that has a central processing unit, a memory, an external storage device, an input device, and an output device. Further, an encoder 19 is disposed adjacent to the endless track 14, so that the encoder 19 detects the amount of movement of the endless track 14. The amount of movement detected by the encoder 19 is transmitted to the control device 20. The detection signals detected by the photoelectric sensor 18 are transmitted to the control device 20. The control device 20 drives the multi-joint arm based on the detection signals detected by the photoelectric sensor 18 and the amount of movement of the clamper 16 detected by the encoder 19 to suspend the work W from the clamper 16 at the right timing. From the clamper 16, a left arm part or a right arm part is suspended at random.

Figure 4A:
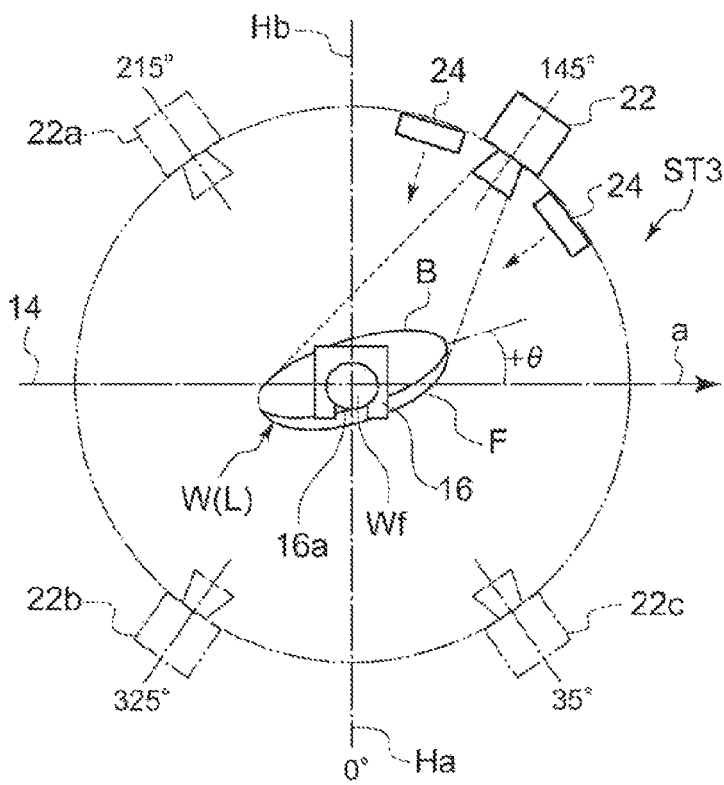
FIG. 4A is an explanatory diagram of imaging procedures of a left arm part in the deboning apparatus.
Figure 4B:
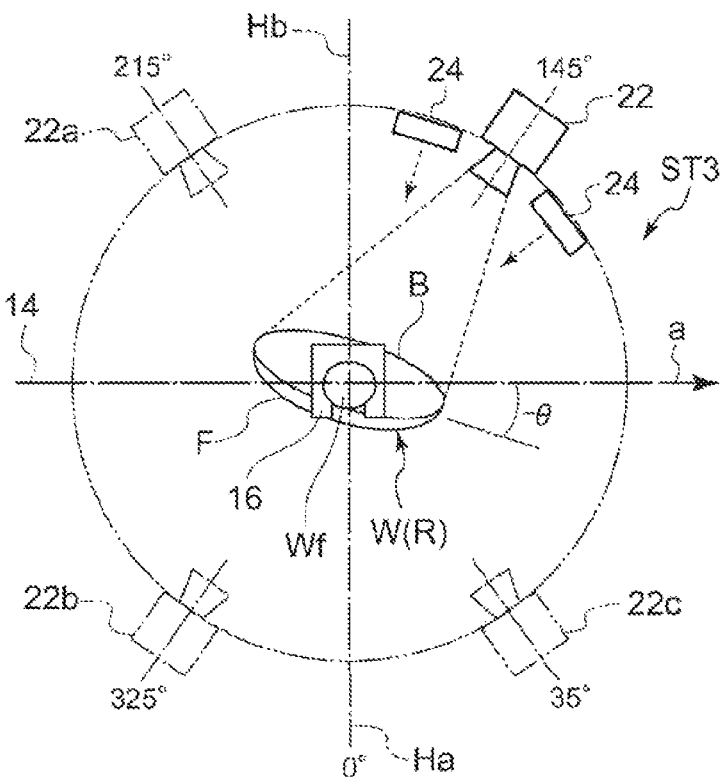
FIG. 4B is an explanatory diagram of imaging procedures of a right arm part in the deboning apparatus.

A left/right determination station ST3 is disposed adjacent to the suspension station ST2 at its downstream side relative to the movement direction of the endless track 14. FIGS. 4A and 4B are schematic diagrams in the planar view of the left/right determination station ST3. FIG. 4A illustrates a suspension state of a left work W (L), which is a left arm part of a pig carcass, and FIG. 4B illustrates a suspension state of a right work W (R), which is a right arm part of a pig carcass. A work W has a back-side portion B whose meat part is exposed at a root portion adjacent to a shoulder part, and a front-side portion F whose skin is adhering to the surface or is removed depending on the type of pre-processing, as described above. In FIGS. 4A and 4B, the arrow "a" indicates the movement direction of the endless track 14.

On the left/right determination station ST3, a CCD camera 22 capable of capturing a color image is disposed on a position where the CCD camera 22 forms an angle of 145° with respect to one orthogonal line Ha of orthogonal lines that are orthogonal to the endless track 14 (an angle of 35° with respect to the other orthogonal line Hb). Further, a plurality of imaging lights 24 for radiating white visible light on the work W are disposed around the CCD camera 22. In FIG. 4A, the left work W (L) is suspended from the clamper 16 at the suspension station ST2 and then naturally rotates by +θ from the endless track 14 due to the shape of the wrist part Wf.

On the other hand, as illustrated in FIG. 4B, the right work W (R) naturally rotates by −θ with respect to the endless track 14 due to the shape of the wrist part Wf, i.e., by the same angle as that in the case of the left work W (L) but in the opposite direction. From the experiments conducted by the present inventors and the like, it has been found that the range of θ falls in the range of [35±20]° with respect to the endless track 14. At the left/right determination station ST3 the left/right determination and front/back determination are performed on the work W using a left/right determination device 40 which will be described below.

A clamper rotating device 26 is disposed downstream in the movement direction of the endless track 14 with respect to the left/right determination station ST3. An X-ray imaging station ST4 is disposed on a downstream side with respect to the clamper rotating device 26. The configuration of the X-ray imaging station ST4 will be described below in reference to FIG. 5. The X-ray imaging station ST4 has an X-ray irradiation device 28, which includes an X-ray source 30 and an X-ray filter 32. Further, the X-ray imaging station ST4 has a shielding box 34 which accommodates the work W being an imaging target of an X-ray image, and a line sensor 36 as an X-ray detector is disposed in the shielding box 34. An X-ray image of the work W is captured at the X-ray station ST4.

The X-ray source 30 and the line sensor 34 are spaced apart from each other across the endless track 14 in a horizontal direction orthogonal to the endless track 14. The X-ray filter 32 applies an intensity distribution of X-rays "x" so that a thick part of the work W is irradiated by a strong X-ray "x" and a thin part of the work W is irradiated by a weak X-ray. The X-ray image of the work W captured at the X-ray imaging station ST4 is analyzed by the control device 20 to determine a target coordinate of a bone-part surface required for incision making in the downstream process. The irradiating direction of the X-rays "x" is orthogonal to the endless track 14.

Figure 5:
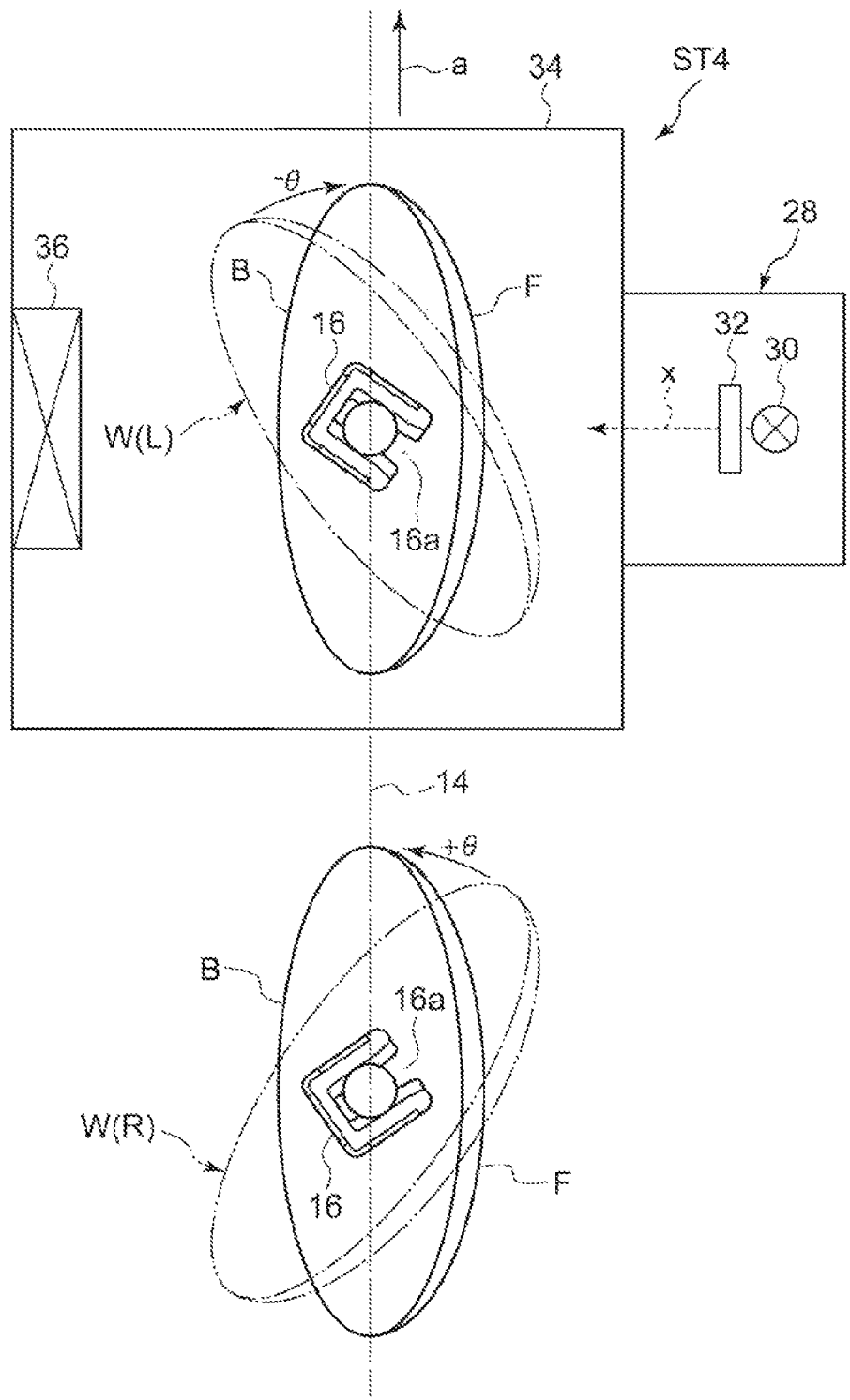
FIG. 5 is a schematic diagram of an X-ray imaging device of the deboning apparatus.

The clamper 16 from which the work W is suspended is rotated about the vertical axial line by the clamper rotating device 26 before arriving at the X-ray imaging station ST4. That is, as illustrated in FIG. 5, the clamper 16 is rotated based on the results determined at the left/right determination station ST3, so that the front-side portion F of the work W is oriented to face the side to which the X-rays "x" are radiated and a longer side of the work W coincides with the endless track 14. In this specification, this posture is referred to as a posture facing directly into the X-rays "x".

A round-blade cutter 38 for making incision around the wrist part Wf is disposed downstream in the movement direction of the endless track 14 with respect to the X-ray imaging station ST4. A first incision-making station ST5 where incision making is performed on the work W in the longitudinal direction is disposed downstream the round-blade cutter 38. Other incision making station and deboning station are disposed downstream the first incision-making station ST5. The control device 20 controls operations of the above. The work W undergoes processes such as incision making and deboning at these stations based on the target coordinate decided by the X-ray imaging to be separated into bone parts and meat parts. The separated bone parts and meat parts are separately discharged from the clamper 16. The clamper 16 that has become empty returns to the suspension station ST2, where another work W would be suspended (for details of the deboning apparatus, see specification and drawings of Japanese patent application No. 2012-56287, which is not yet published at the time of filing of this invention).

Figure 6:
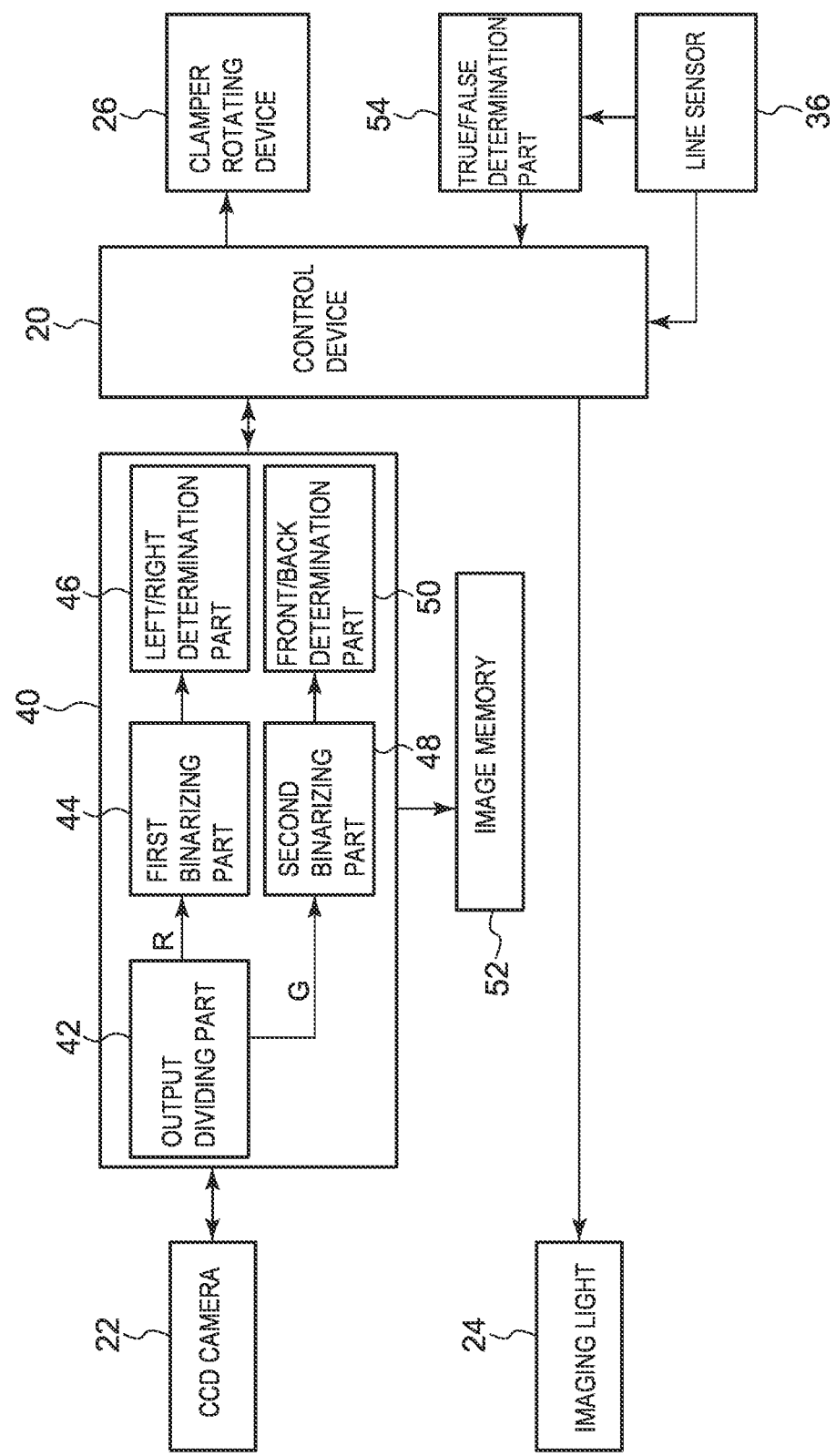
FIG. 6 is a block diagram of a control system and image processing devices of the deboning apparatus.
Figure 7:
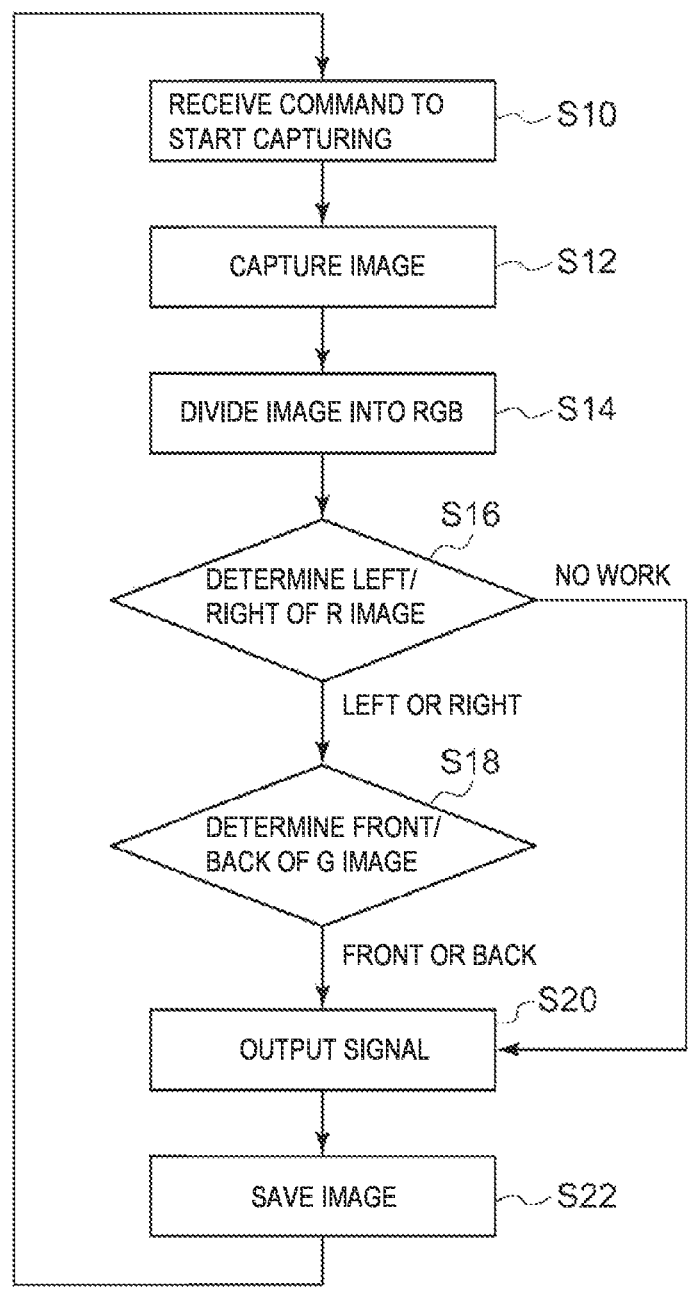
FIG. 7 is a flowchart of operating procedures of the deboning apparatus.

Next, a control system of the deboning apparatus 10 and a configuration of an image processing device 40 that performs left/right determination and front/back determination by processing images captured by the CCD camera 20 will be described in reference to FIG. 6. The determination procedures of the above determinations will be described in reference to FIG. 7. Once the amount of movement of the endless track 14 detected by the encoder 19 reaches a set amount, the control device 20 transmits a trigger signal for starting to capture an image to the CCD camera 20, and then the capturing of an image is started (S10). The imaging lights 24 irradiate the work W with white visible lights and the CCD camera 20 captures an image of the work W in response to a command to start to capture an image (S12).

Figure 8A:
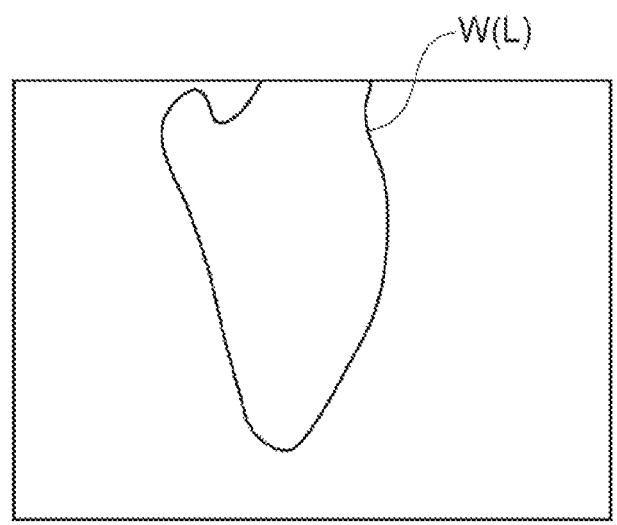
FIG. 8A is an explanatory diagram of an image for left/right determination of a left arm part obtained by the deboning apparatus.
Figure 8B:
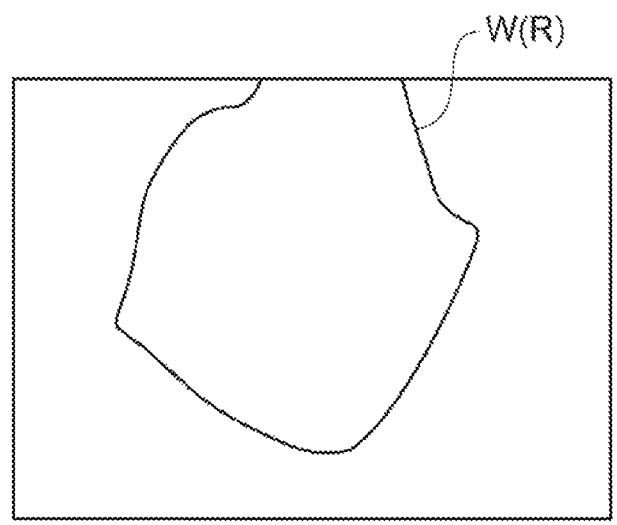
FIG. 8B is an explanatory diagram of an image for left/right determination of a right arm part obtained by the deboning apparatus.

The captured image is transmitted to the left/right determination device 40. The image transmitted to the left/right determination device 40 is then transmitted to an output extracting part 42. The output extracting part 42 divides this image into image signals of the three primary colors of the RGB representation type, which are R (red), G (green), and B (blue) (S14). A first binarizing part 44 binarizes the R image signals outputted from the output extracting part 42. The left/right determination part 46 determines left or right based on the size of an R image region represented by the R image signals after being binarized (S16). The R image signals are used here because the G image signals and the B image signals cause meat parts (lean meat parts and fat parts) to appear dark and thus are not suitable for binarizing. FIG. 8A is an R image of the left work W (L) after binarizing and FIG. 8B is an R image of the right work W (R) after binarizing.

As illustrated in FIG. 4, after being suspended at the suspension station ST2, the left work W (L) naturally rotates by +θ (e.g. +35°) with respect to the endless track 14 while the right work W (R) naturally rotates by −θ (e.g. −35°) with respect to the endless track 14. Thus, there is an apparent difference in size of the R image regions between the left work W (L) and the right work W (R) as illustrated in FIG. 8.

Next, the G image signals are transmitted from the output extracting part 42 to the second binarizing part 48, and the second binarizing part 48 binarizes the G image signals. The front/back determination part 50 determines whether the image is of a front-side portion F or a back-side portion B of the work W from the binarized image (S18). FIGS. 9A and 9B illustrate images of the right work W (R) binarized by the second binarizing part 48 as an example. FIG. 9A is an image of the back-side portion B of the right work W (R) and FIG. 9 B is an image of the front-side portion F of the right work W (R). The red meat parts show many R image signals and few G image signals. In FIGS. 9A and 9B, a shaded area indicates the region with many R image signals, and thus the shaded area represents the red meat parts. In the case where a region of meat parts is large, it is determined to be a back-side portion B. In the case where the region of meat parts is small, it is determined to be a front-side portion F.

The results determined in S16 and S18 are transmitted to the control device 20 (S20). Here, upon determination in S16, there may be occasionally obtained a result of determination indicating that there is no work W suspended from the clamper 16. Such a result of determination is included and also transmitted to the control device 20 in S20. FIG. 10 illustrates an example of the results of determination transmitted to the control device 20. These results of determination are stored in an image memory 52 (S22).

Based on the results of left/right determination and front/back determination of the work W, the control device 20 rotates the clamper rotating device 26 so that the work W is in a posture facing directly into the side irradiated by the X-rays. That is, as illustrated in FIG. 4, when the front-side portion F of the work W is facing the side irradiated by the X-rays, the left work W (L) may be rotated by −θ in the case of the left work W (L) and the right work W (R) may be rotated by +θ in the case of the right work W (R). Also, when it is determined that the back-side portion B is facing the side irradiated by the X-rays from the result of front/back determination, the control device 20 rotates the work W further by 180°. That is, based on the results of left/right determination and front/back determination, a rotation angle that is to be a target for the clamper 16 is set, and then the clamper 16 is rotated by the target rotation angle. In this state, the work W is conveyed to the X-ray imaging station ST4.

At the X-ray imaging station ST4, the X-rays are radiated from the direction of the orthogonal line Ha (the direction of 0°) in FIG. 4. The work W is irradiated with the X-rays in a state of being in the posture facing directly into the side irradiated by the X-rays. The X-ray image detected by the line sensor 34 is transmitted to the control device 20 and analyzed by the control device 20, so that a target coordinate of a bone-part surface required for the incision making step and deboning step in the downstream process is determined.

Further, the X-ray image detected by the line sensor 34 is transmitted to a true/false determination part 54. The true/false determination part 54 performs normal image process including binarizing and the like on the X-ray image detected by the line sensor 34, so as to obtain directions of the clamper 16 and the work W. Then, based on the obtained directions of the clamper 16 and the work W, the true/false determination part 54 checks whether the left/right determination and front/back determination by the left/right determination device 40 are true or false. That is, when the result of left/right determination by the left/right determination device 40 is false, the work W is not facing directly into the side irradiated by the X-rays. Thus, such an image may not be obtained that represents a bone-part surface required for the incision making step and deboning step in the downstream process. Also, when the result of front/back determination is false, the incision making process and deboning process may not be accurately performed in the deboning step. When it is determined that the result of left/right determination or front/back determination is false by the true/false determination part 54, the accordingly determined work W is omitted from a deboning process line at an exit of the X-ray imaging station ST4 by the control device 20.

According to the present embodiment, it is possible to perform left/right determination and front/back determination on the work W at the same time and in one step immediately and accurately while the work W is being suspended from the clamper 16. Thus, it is possible to improve deboning processing efficiency in the deboning process of the deboning apparatus 10. Further, by performing left/right determination and front/back determination, it is possible to accurately obtain the posture of the work W suspended from the clamper 16, which enables accurate incision making process and deboning process in the downstream process, and thus enables improving yields in the deboning process.

Further, by detecting whether the work W is suspended from the clamper 16 by the photoelectric sensor 18, it is possible to start to capture an image of the work W in accordance with the timing at which the work W is suspended from the clamper 16. Thus, it is possible to start left/right determination and front/back determination timely and immediately.

Still further, it is possible to determine whether the results of left/right determination and front/back determination determined at the left/right determination station ST3 are true or false by the true/false determination part 54 at the X-ray imaging station ST4. Then, when the X-ray image required for the incision making step and deboning step in the downstream process may not be obtained, it is possible to omit the work W from the deboning process line at the exit of the X-ray imaging station ST4. As a result, an event such as stop of operation of the deboning apparatus 10 is avoided.

Moreover, when it is determined that the back-side portion B of the work W is facing the X-ray irradiating direction by the front/back determination part 50 of the left/right determination device 40, the clamper rotating device 26 is driven by the control device 20 to rotate the work W further by 180°, which makes it possible to orient the work W to face directly into the X-ray irradiating direction. As a result, it is possible to obtain the X-ray image required for the incision making step and deboning step in the downstream process and thus to improve the deboning process efficiency.

In addition, the arrangement of the CCD camera 22 is not limited to the direction of 145° from the orthogonal line Ha, and may be in the range of [145±20]°. Further, as illustrated in FIG. 4 with references 22a to 22c, the CCD camera 22 may be disposed in the range of [215±20]°, the range of [325±20]°, or the range of [35±20]° with respect to the orthogonal line Ha. Also, instead of disposing the photoelectric sensor 18 on the downstream end of the pre-processing station ST1, a photoelectric sensor 18' may be disposed on a downstream end of the suspension station ST2 to detect whether the work W is suspended from the clamper 16 after the work W has been suspended. Alternatively, instead of the photoelectric sensor 18, a limit switch 19 may be disposed on an inner portion of the slit 16a of the clamper 16, and the limit switch 19 may detect whether the work W is suspended from the clamper 16.

Further, instead of providing the true/false determination part 54, the results of left/right determination and front/back determination of the work W may be determined to be true or false by an operator visually checking an X-ray image detected by the line sensor 34 at the X-ray imaging station ST4. Then, when the result of left/right determination or front/back determination is false, the operator may operate the control device 20 to omit the work W whose result of determination is false from the deboning process line.

INDUSTRIAL APPLICABILITY

According to the present invention, since it is possible to perform left/right determination of an arm part of a pig carcass accurately while the arm part is being suspended from a clamper, it is possible to improve efficiency in a deboning process when applied to a deboning process line or the like.

The invention claimed is:

1. A left/right determination system for an arm part of a pig carcass, comprising:
   a clamper including a slit which has an opening oriented in a horizontal direction so that a wrist part of a pig carcass is insertable into or removable from the slit, the clamper being configured to be movable along a track in a state where the arm part of the pig carcass is suspended from the clamper;
   a light source configured to radiate white visible light on the arm part suspended from the clamper;
   a color imaging device configured to capture an image of the arm part being irradiated with the white visible light from an inclined horizontal direction which is inclined relative to the horizontal direction in which the opening of the slit is oriented; and
   a left/right determination device configured to determine whether the arm part is of a left arm or a right arm based on an image data of the arm part captured by the color imaging device,
   wherein the left/right determination device comprises:
      an output extracting part configured to extract red image signals which correspond to a red wavelength range from the image data;
      a first binarizing part configured to binarize the red image signals extracted by the output extracting part; and
      a left/right determination part configured to determine whether the arm part is of a left arm or a right arm based on the red image signals binarized by the first binarizing part.

2. The left/right determination system for an arm part of a pig carcass according to claim 1,
   wherein the opening of the slit of the clamper is oriented in a direction orthogonal to the track while the color imaging device is capturing the image, and
   wherein the inclined horizontal direction from which the color imaging device is configured to capture the image forms an angle of not less than 15° and not greater than 55° with respect to the track.

3. The left/right determination system for an arm part of a pig carcass according to claim 1,
   wherein the output extracting part is capable of extracting non-red image signals which correspond to a wavelength range other than the red wavelength range from the image data, and
   wherein the left/right determination device further comprises:
      a second binarizing part configured to binarize the non-red image signals extracted by the output extracting part; and
      a front/back determination part configured to determine whether a front side or a back side of the arm part is facing the color imaging device based on a distribution of the non-red image signals binarized by the second binarizing part.

4. The left/right determination system for an arm part of a pig carcass according to claim 1, further comprising:
   a suspending device configured to suspend the arm part from the clamper at an upstream position relative to a position where the color imaging device captures the image;
   a detector configured to detect whether the arm part is suspended from the clamper; and
   a first control device configured to cause the color imaging device to start to capture the image of the arm part upon receiving a suspension signal transmitted from the detector.

5. The left/right determination system for an arm part of a pig carcass according to claim 1, further comprising:
   an X-ray imaging device configured to radiate an X-ray on the arm part to obtain an X-ray image at a downstream position relative to the position where the color imaging device captures the image;
   a clamper rotating device configured to rotate the clamper about a vertical axial line between the position where the color imaging device captures the image and a position where the X-ray imaging device captures the image; and
   a second control device configured to set a target value of a rotation angle based on a result of left/right determination of the arm part determined by the left/right determination device to drive the clamper rotating device so that the clamper is rotated by the set target value.

6. The left/right determination system for an arm part of a pig carcass according to claim 5,
   wherein the second control device is configured to set a target value of a rotation angle based on the result of left/right determination and a result of front/back determination determined by the left/right determination device to drive the clamper rotating device so that the clamper is rotated by the set target value.

7. The left/right determination system for an arm part of a pig carcass according to claim 6, further comprising
   a true/false determination device configured to determine whether the result of left/right determination and the result of front/back determination determined by the left/right determination device are true or false based on a direction of the clamper and a direction of the arm part in the X-ray image obtained by the X-ray imaging device.

* * * * *